(12) United States Patent
Ivansons et al.

(10) Patent No.: US 7,398,813 B2
(45) Date of Patent: Jul. 15, 2008

(54) DEVICE FOR WELDING PLASTIC TUBES

(75) Inventors: Ivars V. Ivansons, Elkton, MD (US);
Gregory M. Bak, Claymont, DE (US);
Dudley Spencer, Wilmington, DE (US)

(73) Assignee: Denco Inc., Wilmington, DE (US)

( * ) Notice: Subject to any disclaimer, the term of this patent is extended or adjusted under 35 U.S.C. 154(b) by 23 days.

(21) Appl. No.: 11/496,282

(22) Filed: Jul. 31, 2006

(65) Prior Publication Data

US 2008/0023135 A1   Jan. 31, 2008

(51) Int. Cl.
*B32B 37/00* (2006.01)
(52) U.S. Cl. .................. 156/499; 156/503; 156/507; 156/510
(58) Field of Classification Search ................. 156/157, 156/158, 304.2, 304.5, 304.6, 499, 502, 503, 156/507, 510, 258
See application file for complete search history.

(56) References Cited

U.S. PATENT DOCUMENTS

| | | |
|---|---|---|
| 4,610,670 A | 9/1986 | Spencer |
| 4,619,642 A | 10/1986 | Spencer |
| 4,770,735 A | 9/1988 | Shaposka |
| 4,793,880 A | 12/1988 | Shaposka |
| 4,832,773 A | 5/1989 | Shaposka |
| 4,864,101 A | 9/1989 | Shaposka |
| 4,897,138 A | 1/1990 | Shaposka |
| 4,913,756 A | 4/1990 | Shaposka |
| 4,929,293 A | 5/1990 | Osgar |
| 4,933,036 A | 6/1990 | Shaposka |
| 5,141,592 A | 8/1992 | Shaposka |
| 5,156,701 A | 10/1992 | Spencer |
| 5,158,630 A | 10/1992 | Shaposka |
| 5,209,800 A | 5/1993 | Spencer |
| 5,244,522 A | 9/1993 | Spencer |
| 5,248,359 A | 9/1993 | Shaposka |
| 5,256,229 A | 10/1993 | Spencer |
| 5,279,685 A | 1/1994 | Ivansons |
| 5,397,425 A | 3/1995 | Ivansons |
| 5,525,186 A | 6/1996 | Ivansons |
| 5,632,852 A | 5/1997 | Ivansons |
| 5,674,333 A | 10/1997 | Spencer |
| 5,855,731 A | 1/1999 | Spencer |
| 5,871,612 A | 2/1999 | Spencer |

(Continued)

OTHER PUBLICATIONS

International Search Report dated Jan. 18, 2008 for PCT/US/07/73651.

*Primary Examiner*—James Sells
(74) *Attorney, Agent, or Firm*—Connolly Bove Lodge & Hutz LLP

(57) ABSTRACT

Plastic tubes are welded by first placing the plastic tubes across aligned tube slots in a pair of side by side tube holders. The tubes are clamped to create a fluid free area. The clamps in one of the tube holders are shifted laterally away from the other tube holders to increase the fluid free area of each tube. A cold cutting device cuts through the clamped tubes to create four stub ends. The four stub ends are heated/melted. The stub ends are realigned so that the one stub end in one holder is aligned with the other stub end of the other tube holder and the realigned stub ends are pressed into contact with each other to create a weld seam.

25 Claims, 9 Drawing Sheets

U.S. PATENT DOCUMENTS

| | | |
|---|---|---|
| 6,020,574 A | 2/2000 | Ivansons |
| 6,132,833 A | 10/2000 | Spencer |
| 6,177,652 B1 | 1/2001 | Ivansons |
| 6,341,637 B1 * | 1/2002 | Yamada et al. ............... 156/433 |
| 6,460,592 B1 | 10/2002 | Sano |
| 6,463,979 B1 * | 10/2002 | Sano et al. .................. 156/503 |
| 6,637,489 B1 | 10/2003 | Spencer |
| 6,913,056 B2 | 7/2005 | Landherr et al. |
| 6,926,189 B2 * | 8/2005 | Shanks et al. ............ 228/173.4 |

* cited by examiner

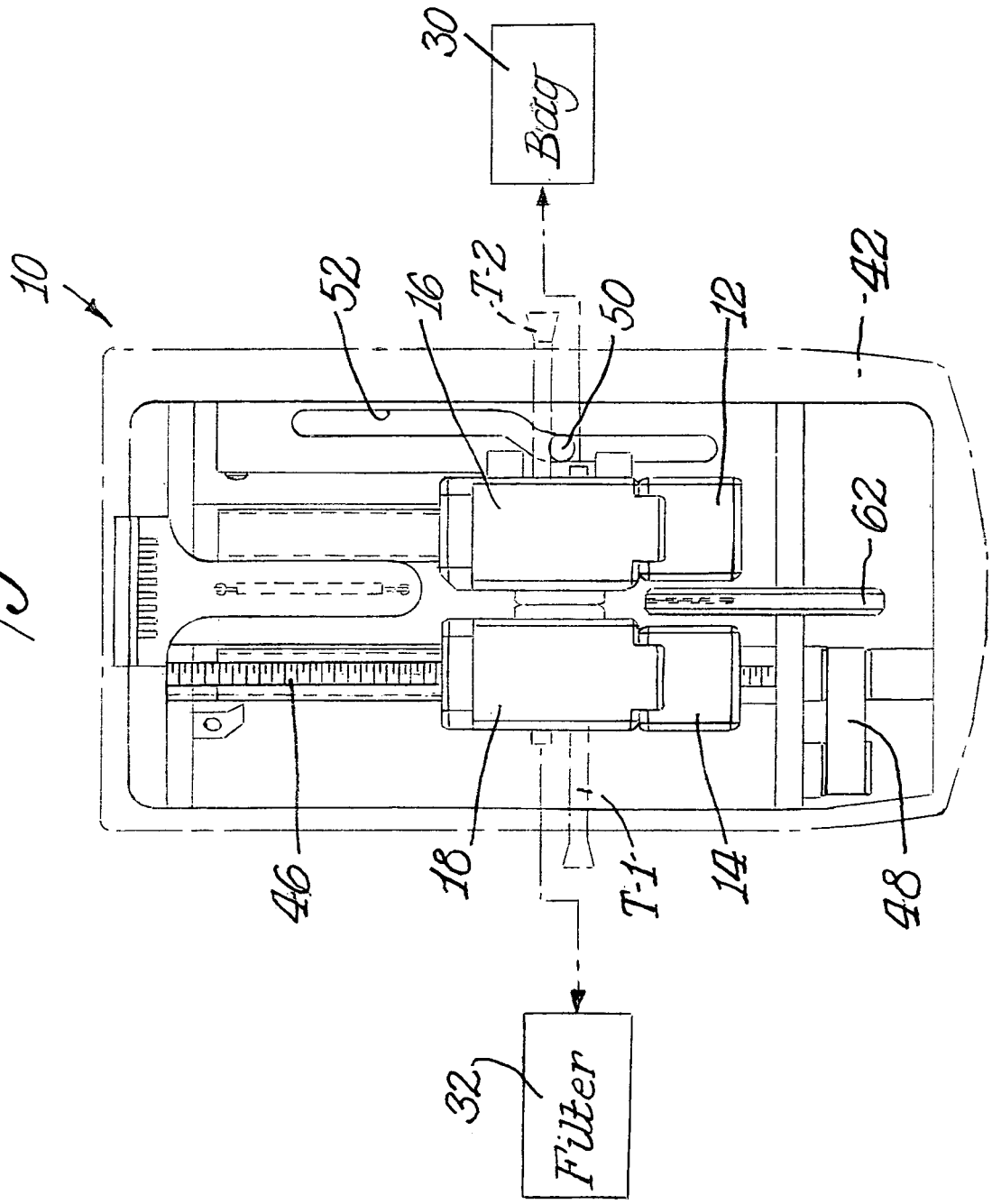

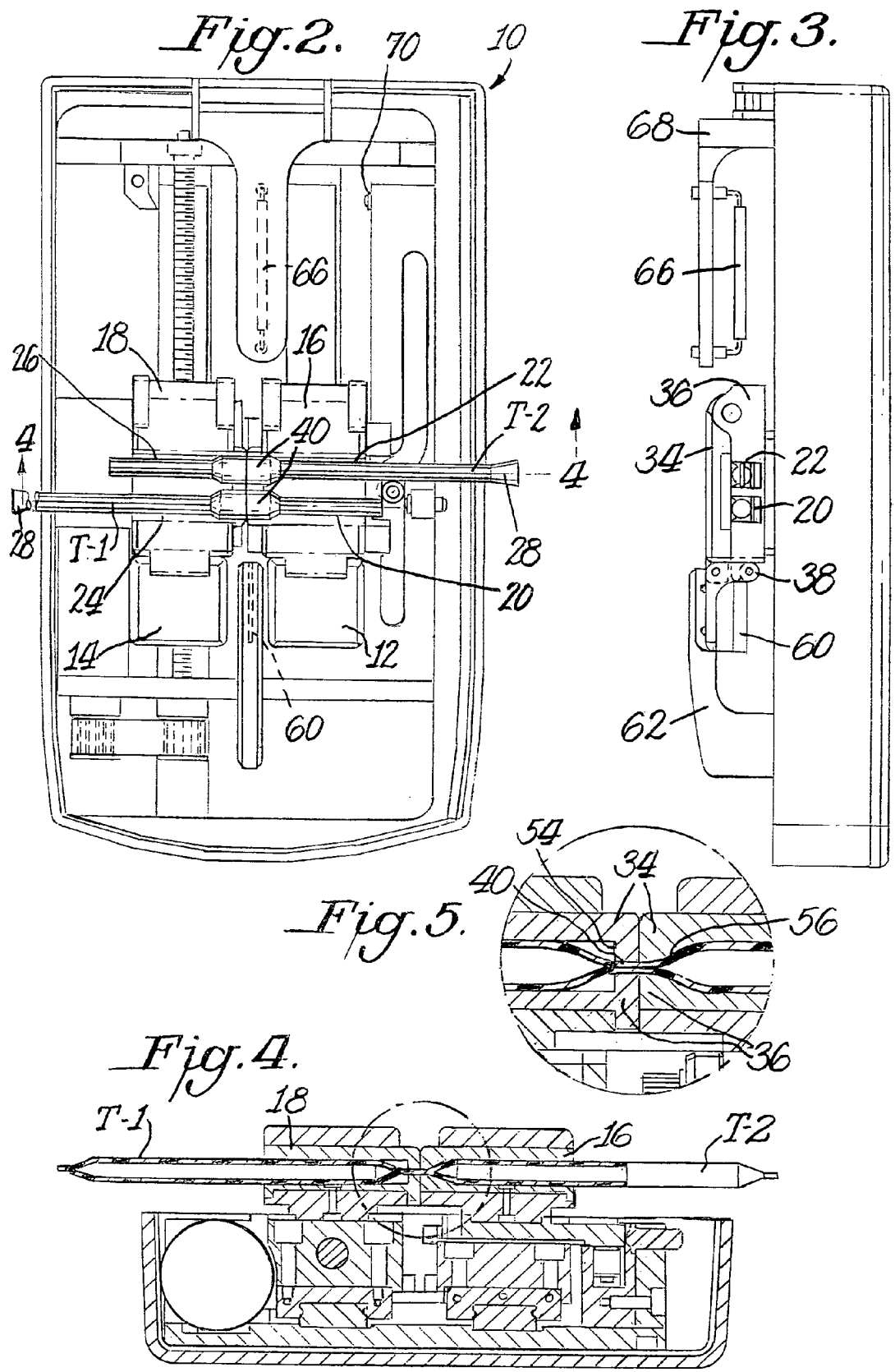

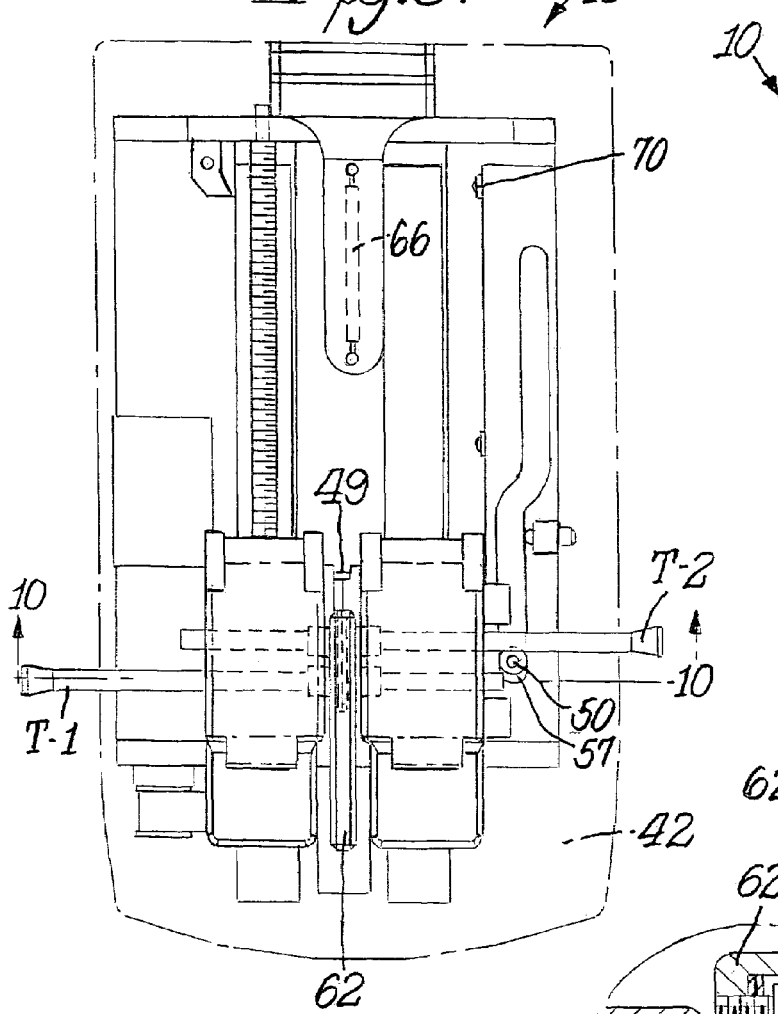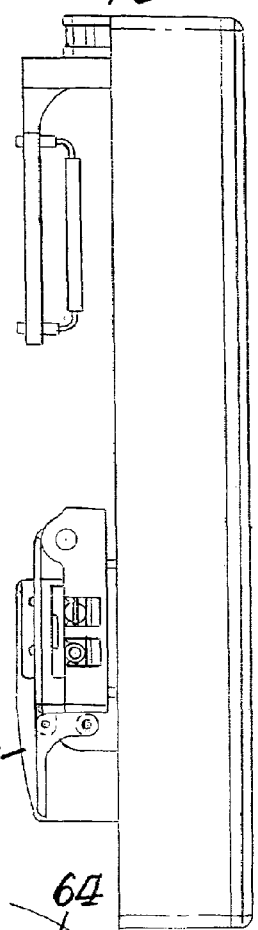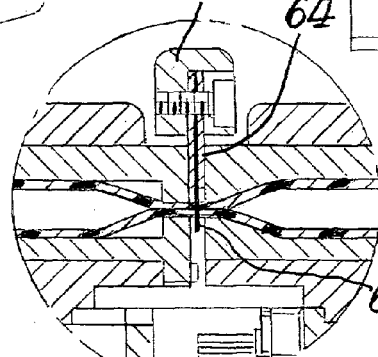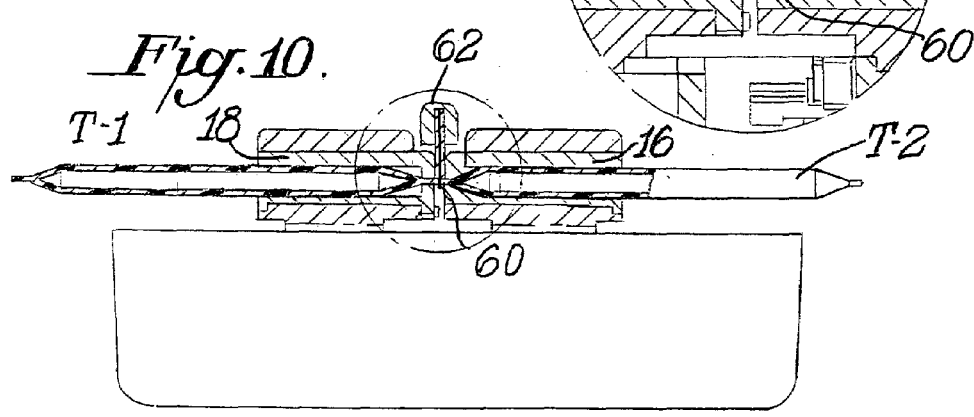

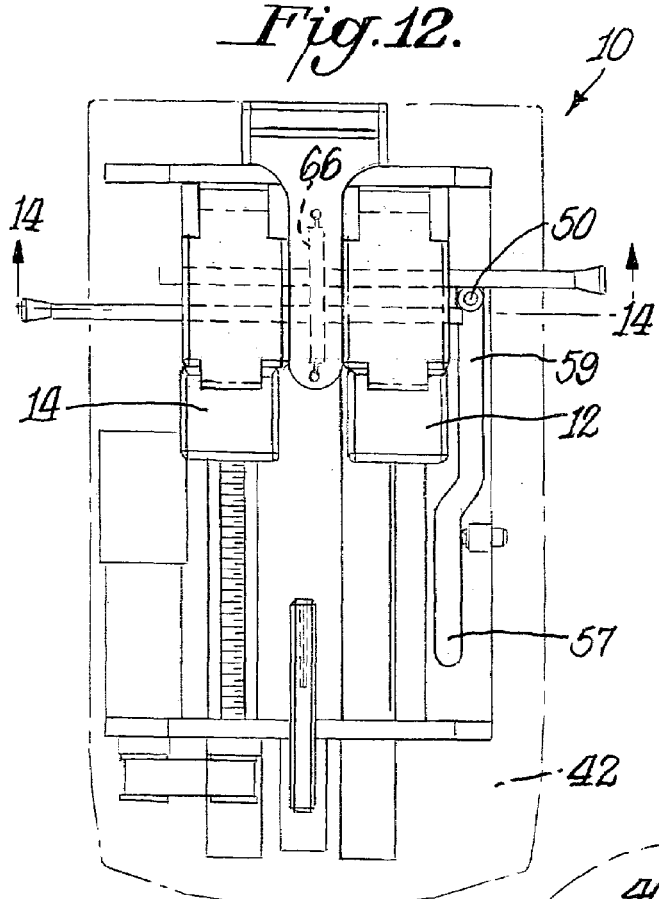
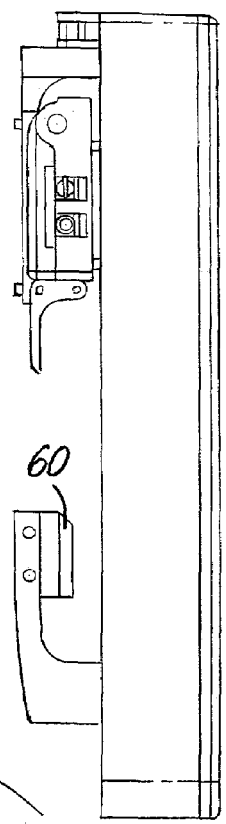
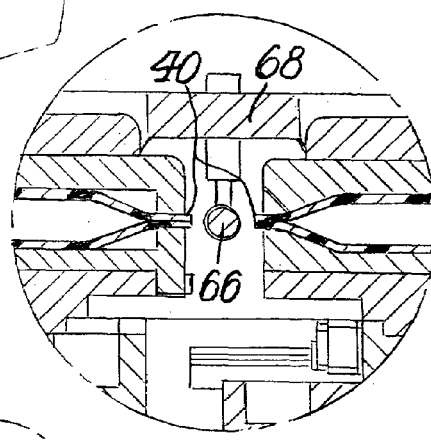
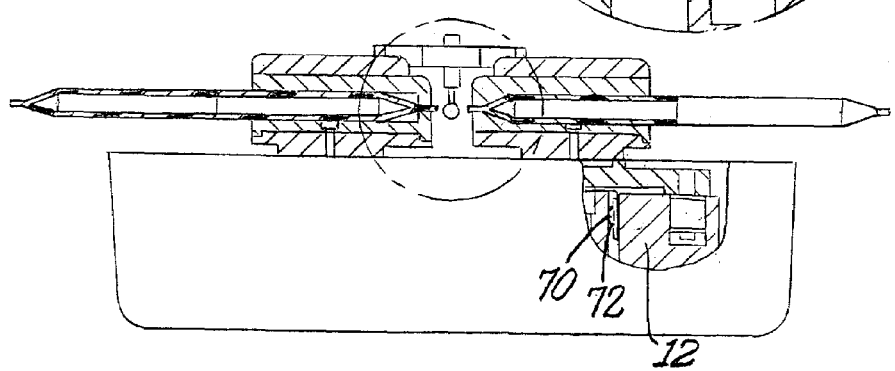

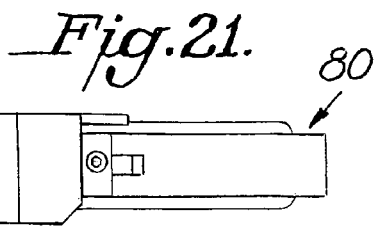
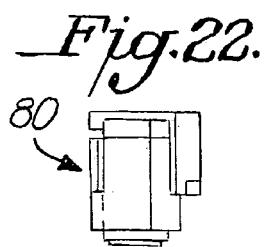
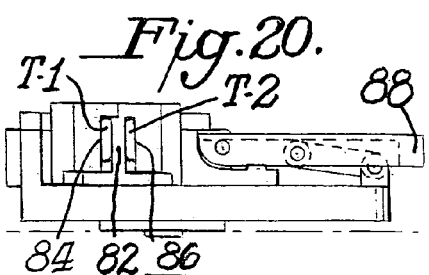
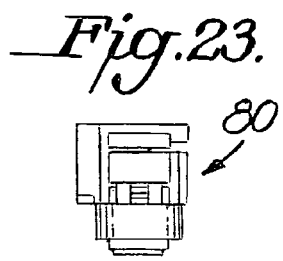
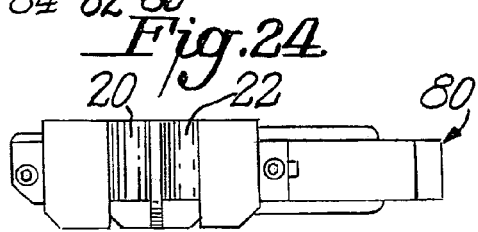
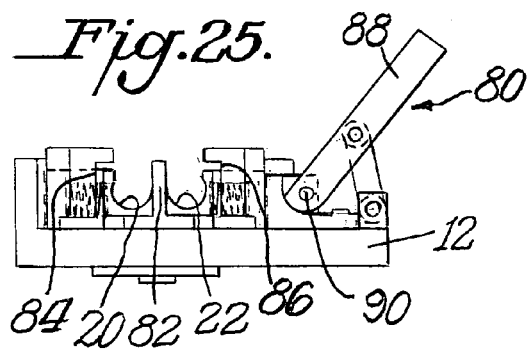

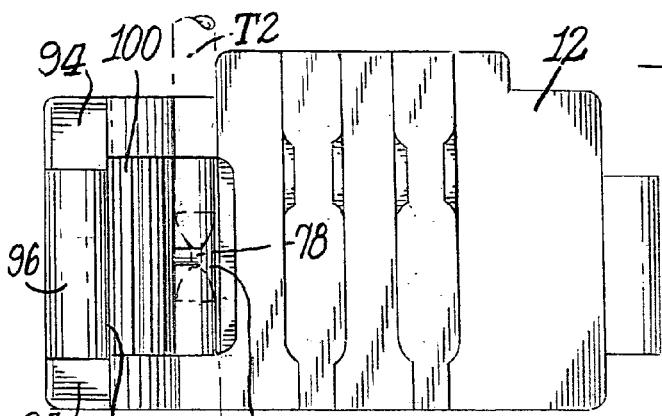
Fig. 27.
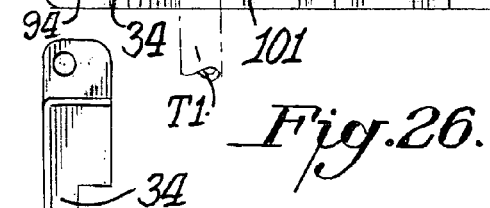
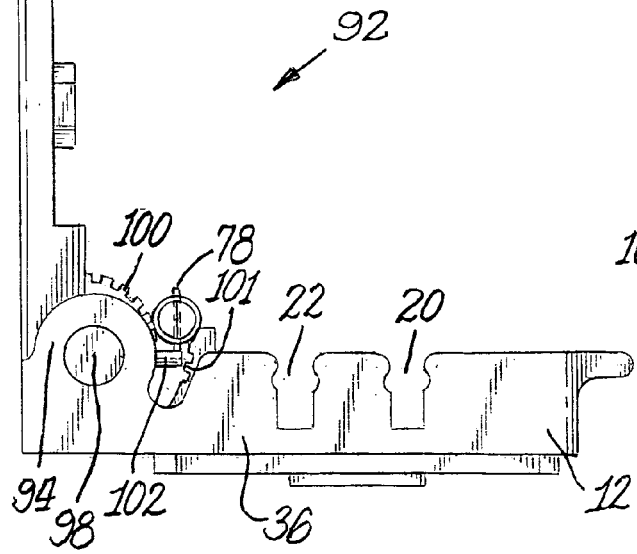
Fig. 26.
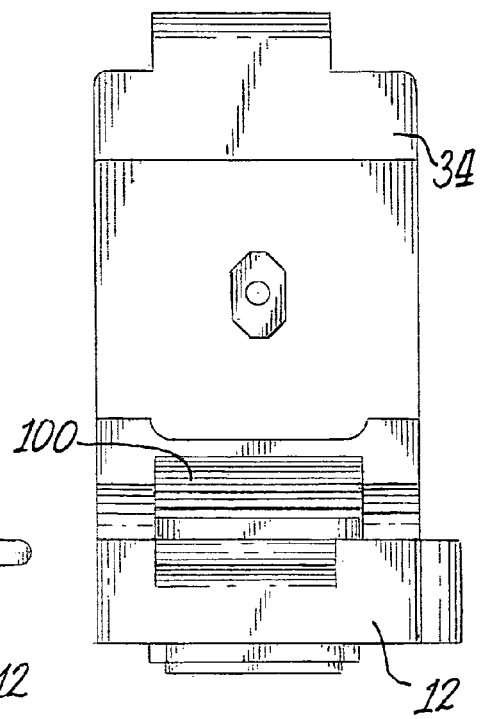
Fig. 28.
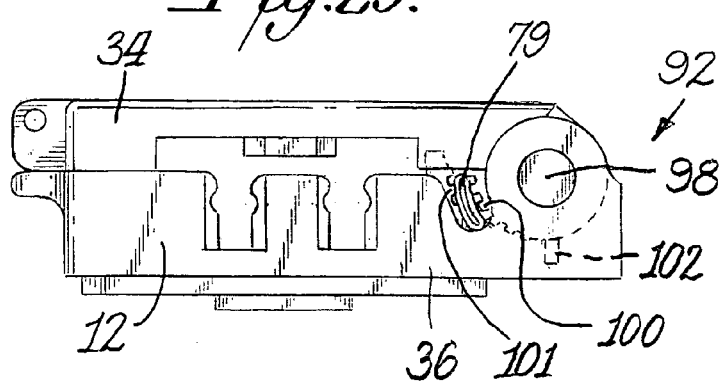
Fig. 29.

DEVICE FOR WELDING PLASTIC TUBES

BACKGROUND OF THE INVENTION

Various techniques have been used for welding plastic tubes, particularly as used in the medical field. For example, there are situations where medical or scientific procedures require sterile transfer of dangerous or sensitive fluids from one container to another. For example, in continuous ambulatory peritoneal dialysis (CAPD) the procedure involves replacing hemo-dialysis. The CAPD patient has a tube connected to the patient's peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period the empty bag is folded and carried by the patient who can continue with his or her normal activities. After this treatment period the spent dialysate is drained back into the empty bag which is then disconnected from the patient's tube. A bag of fresh dialysis solution is then connected to the patient's tube and the procedure is repeated. In this connection process the tube from the new bag is to be welded to the tube leading from the patient so that the new bag can replace the used bag. This process involves cutting the tubes of both bags and then welding the tube from the new bag to the tube from the patient. Similar techniques which require cutting plastic tubes and then welding a portion of one tube to another tube includes such processes as blood processing, bio-medical technology labs, total parenteral feeding, chemotherapy, urinary drainage and indwelling catheters.

A common technique used for the cutting of the plastic tubes and then welding the tubes together utilizes a heated wafer which cuts through a pair of tubes either simultaneously or sequentially. The heated tube ends are in a molten condition so that by shifting the tubes a molten tube end from one of the tubes is disposed inline with a molten tube end from the other tube. The molten ends are pressed together to weld the two tube sections and form a unitary tube. U.S. Pat. Nos. 4,610,670; 4,619,642; 4,770,735; 4,793,880; 4,832,773; 4,864,101; 4,897,138; 4,913,756; 4,933,036; 5,141,592; 5,156,701; 5,158,630; 5,209,800; 5,244,522; 5,248,359; 5,256,229; 5,279,685; 5,397,425; 5,525,186; 5,632,852; 5,674,333; 5,855,731; 5,871,612; 6,020,574; 6,132,833; 6,177,652; and 6,637,489 are examples of techniques using heated wafers. All of the details of these patents are incorporated herein by reference thereto.

U.S. Pat. No. 6,913,056 discloses an apparatus and method for connecting and disconnecting flexible tubing without a heated wafer and which involves crimping a tube in guides during the disconnect procedure. A hammer located between the guides moves into contact with the tube pushing liquid out of the area to be disconnected. As the tube is pinched between the hammer and an anvil a laser heats the pinched tube to seal it. The hammer remains in contact with the tube while it cools. The hammer then moves back to its original position and the guides are removed in reverse pulling the tube apart with two sealed ends.

One of the main problems in sterile connection technology has been welding liquid filled tubes. The weld site must be clear and free of any fluid or fluid ingress before a welding process can begin. The prior art techniques for removing and preventing fluid from entering the weld site are generally characterized by intrinsic weakness or are expensive to implement. Some prior techniques involve minimizing clamping distances or registering sealed tube ends to prevent trapping fluid beyond the clamp faces. These techniques work but have a small operating window and cannot guarantee consistent fluid free weld sites. Other methods include the use of rollers or even of creating temporary seals to remove fluids from the weld site prior to completing a weld. While these systems are functional they are difficult and expensive to implement.

SUMMARY OF THE INVENTION

An object of this invention is to provide a device for welding plastic tubes which does not require the use of a heated wafer.

A further object of this invention is to provide such a device for welding plastic tubes which utilizes fluid stripping to increase the amount of fluid free tubing so as to permit the cutting to take place by a cold cut rather than a heated wafer.

In accordance with this invention the device for welding plastic tubes comprises a first tube holder having first and second parallel tube holding areas with a second tube holder having its first and second parallel tube holding areas in line with those of the first tube holder when the tube holders are in a tube loading station. Thus a first tube may be placed in the aligned first tube holding areas across the location where the tube holders are adjacent each other and a second tube may similarly be placed in the aligned second tube holding areas. A tube clamp in each of the first tube holding areas clamps the first tube to create a generally fluid free area of the first tube. At least one of the clamps is laterally movable while the clamps are maintained in their clamping condition to increase the length of the fluid free area of the first tube and thereby create an enlarged gap between the tube clamps. The tube holders are movable to a cutting station while the clamps are maintained in the clamping condition. A non-heated cutting device, such as a cold blade in the cutting station, cuts through the first tube at the gap between the two clamps and also cuts through the second tube thereby creating four cut ends or stubs from the first and second tubes. The tube holders are moved to a heating station with the clamps still maintained in their clamping condition. A heating device heats/melts the cut stub ends of the tubes. The cut ends of the tubes are realigned so that a cut stub end of the first tube becomes aligned with a cut stub end of the second tube and these heated/melted cut stub ends are shifted into contact with each other to become welded together.

In the preferred practice of this invention the second tube, in addition to the first tube, is clamped and at least one of the clamps is moved relative to the other clamp to increase the fluid free area of the second tube. Preferably, the heating is accomplished through use of an infra-red heat source which melts and seals the tube stub ends thereby enabling a sterile closed connection system without the need of a consumable wafer.

THE DRAWINGS

FIG. 1 is a top plan view of a device for welding plastic tubes in accordance with this invention in the tube loading station;

FIG. 2 is a top plan view of the device shown in FIG. 1 with the clamps in an open position;

FIG. 3 is a side elevational view of the device shown in FIG. 2 with the clamps closed;

FIG. 4 is a cross-sectional view taken through FIG. 2 along the line 4-4 with the clamps closed;

FIG. 5 is an enlarged cross-sectional view of the portion of the device shown in the circle in FIG. 4;

FIG. 8 is a top plan view of the device shown in FIGS. 1-7 in the condition where the tubes are cut in the cutting station;

FIG. 9 is a side elevational view of the device shown in FIG. 8;

FIG. 10 is a cross-sectional view taken through FIG. 8 along the line 10-10;

FIG. 11 is a view similar to FIGS. 5 and 7 showing the tubes in the cutting station;

FIG. 12 is a top plan view of the device shown in FIGS. 1-11 in the heating/melting stage;

FIG. 13 is a side elevational view of the device shown in FIG. 12;

FIG. 14 is a cross-sectional view taken through FIG. 12 alone line 14-14;

FIG. 15 is a view similar to FIGS. 5, 7 and 11 showing the tubes in the heating/melting station;

FIG. 20 is a side elevational view of a modified clamp in a closed condition used for large diameter tubes;

FIG. 21 is a top plan view of the clamp shown in FIG. 20;

FIGS. 22-23 are front and rear elevational views of the clamp shown in FIGS. 20-21;

FIG. 24 is a top plan view similar to FIG. 21 with the clamp in an open condition;

FIG. 25 is a side elevational view of the clamp shown in FIG. 24;

FIG. 26 is a front elevational view of a modified form of clamp used for opening a welded tube in accordance with this invention wherein the clamp is in the open condition;

FIG. 27 is a top plan view of the clamp shown in FIG. 26;

FIG. 28 is a top plan view of the clamp shown in FIGS. 26-27 in the closed condition; and FIG. 29 is an end elevational view of the clamp shown in FIGS. 26-28 in the closed condition.

DETAILED DESCRIPTION

Figure 6:
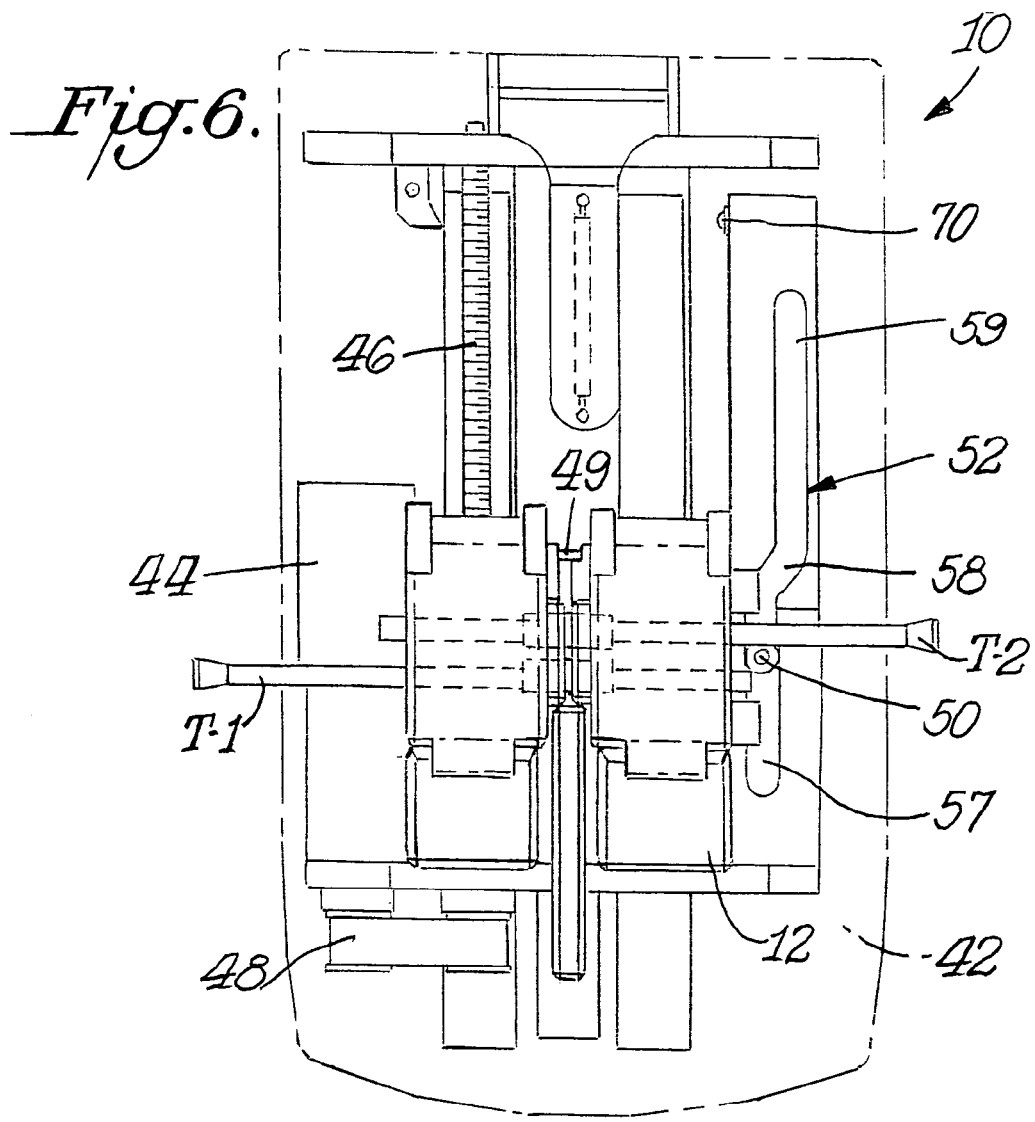
FIG. 6 is a top plan view of the device of FIGS. 1-5 where the clamps have been relatively moved laterally apart in the stripping station.

The present invention, in its preferred embodiment, involves techniques for accomplishing a sterile welding of plastic tubes, particularly wherein at least one of the plastic tubes might contain a fluid. The sterile welding is accomplished without the use of a conventional heated wafer. More particularly, in the preferred embodiment, the plastic tubes are placed in parallel orientation with respect to each other in the tube holding areas of side by side tube holders at a loading station. The tube holders include clamps which compress the tubes to create flattened areas free of any fluid. One of the tube holders is then laterally shifted in a stripping station while the clamps are in their engaged position to increase the fluid free area. The tube holders are then moved longitudinally to a cutting station where the tubes are cut by a cold cutting blade to create four cut or stub ends in the fluid free areas so that each stub end is also free of fluid. The tube holders are again moved longitudinally to a heating/melting station which has a heat source. Preferably, the tube holders are spread further apart to accommodate the heat source being between the four cut stub ends which then heats/melts the stub ends. The direction of longitudinal movement of the tube holders is then reversed. During this reverse movement, however, one of the tube holders is longitudinally shifted so that the tube holding areas become realigned disposing one stub end of one tube in line with a stub end of the other tube. These realigned stub ends are then pressed into contact with each other at a welding station by laterally moving the tube holders toward each other so that the heated/melted stub ends become welded together and form a unitary tube which can be opened by simple finger pressure at the weld site.

FIGS. 1-5 illustrate a device 10 for welding plastic tubes in accordance with a preferred embodiment of this invention. As shown therein, the device is a self-contained unit which has various stations for performing the tube loading, the tube stripping, the tube cutting, the stub end heating/melting and finally the welding of the realigned stub ends. The device 10 could be in the form of a housing having a base or support 42 for the various components and a hinged or removable cover (not shown) mounted to the support 42 during periods of non-use. FIG. 1 illustrates the device in the tube loading condition. As shown therein, a first tube holder 12 and a second tube holder 14 are located side by side. Each tube holder has a clamp 16,18 as later described.

FIG. 1 illustrates the clamps 16,18 in their closed condition. FIG. 2 shows the clamps 16,18 in the open condition. As illustrated, tube holder 12 includes first and second parallel tube holding areas 20,22 in the form of parallel slots that will accommodate the tubes T-1 T-2 to be welded. Similarly, tube holder 14 includes parallel tube holding areas 24,26 which are aligned with the corresponding first and second tube holding areas 20,22 of tube holder 12. Tubes T-1 and T-2 may be used for various known purposes. For example, as illustrated in FIGS. 1 and 2 each tube T-1, T-2 has a sealed end 28. As shown in FIG. 1 tube T-1 communicates with a bag 30 while tube T-2 communicate with a filter 32. Device 10 is used when it is desired to connect the bag 30 with the filter 32. This would necessitate cutting the tubes T-1, T-2 so that the portion of the tube T-1 leading from bag 30 would be connected to the portion of tube T-2 leading from filter 32. Bag 30 and filter 32 exemplify different members each having a tube. Other members, containers, devices, etc. could be used depending on the specific uses for which the invention may apply.

In loading tubes T-1, T-2 each tube is placed into the slots or tube holding areas of each tube holder 12,14 with their sealed ends 28 protruding from the sides of the tube holders 12,14, as shown in FIG. 2.

Clamps 16,18 may take any suitable form. The aforenoted patents describe various clamps which could be used with this invention when used for creating a fluid free area. As illustrated each clamp includes a top half or portion 34 hinged to the bottom half or portion 36 and securely latched by clamp roller latch 38. The spacing between the clamp jaws is set at a fixed height that will compress the tubing so that no fluid will be expelled when the tubing is cut prior to heating and welding.

As shown in FIG. 5 the front face of the tube clamp jaws at upper and lower portions 34,36 are held flush against each other during tube loading to ensure that no fluid is trapped between the clamps. As a result, a fluid free area 40 is formed in each tube in the tube loading station.

It is to be understood that any suitable clamp mechanism may be used in the broad practice of this invention. Such clamp mechanism should have the capability of compressing the tube to form a fluid free area and have the capability of extending that fluid free area when the aligned clamp mechanisms are moved relatively apart in a lateral direction to thereby increase the length of the fluid free area.

Figure 7:
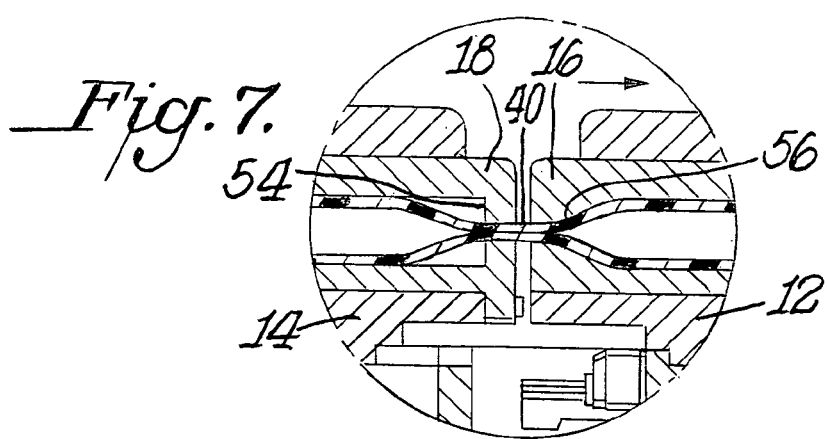
FIG. 7 is a view similar to FIG. 5 of the device in the condition shown in FIG. 6.
Figure 12A:
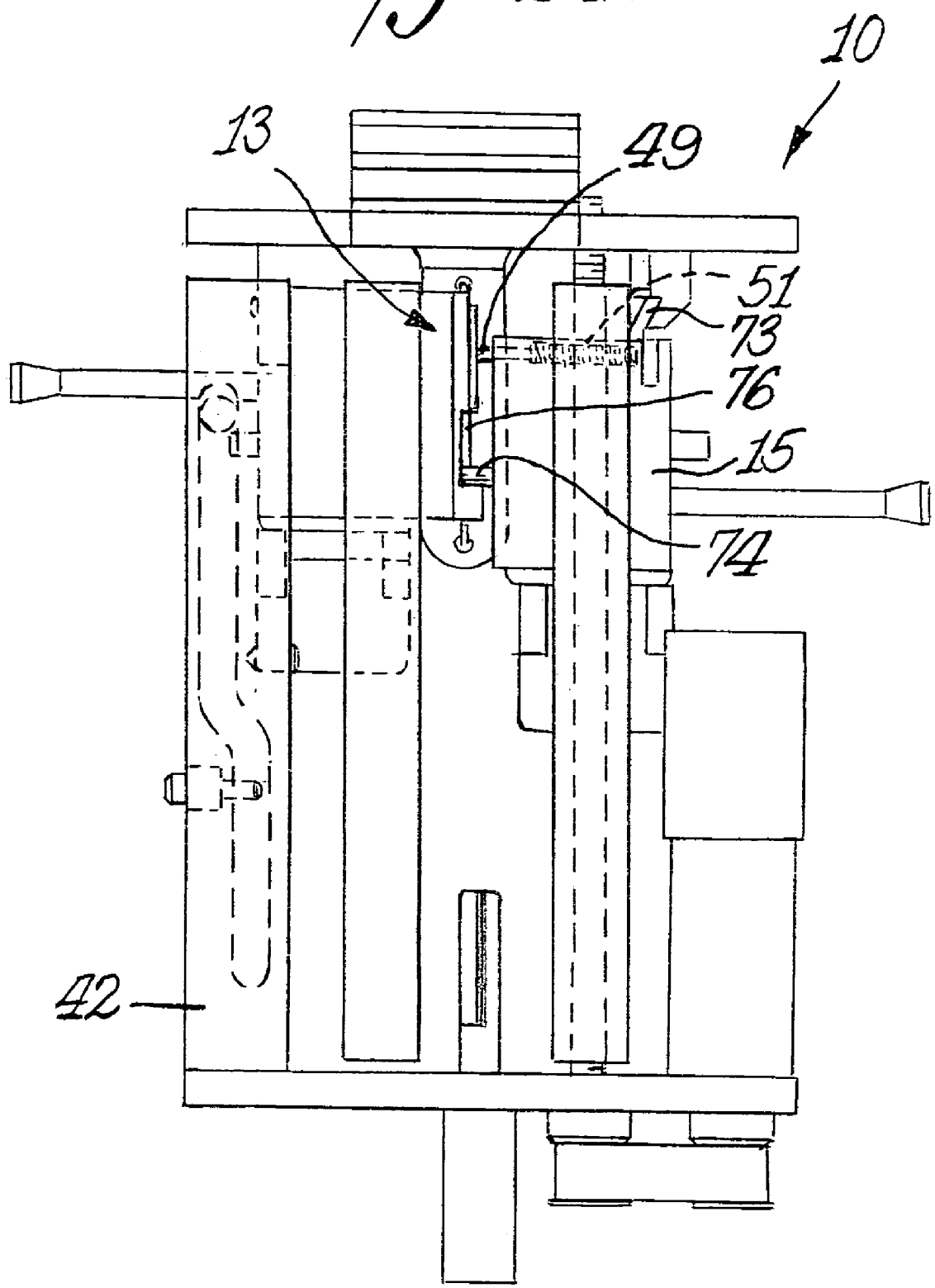
FIG. 12A is a bottom plan view of the device shown in FIGS. 1-12.

FIGS. 6-7 show the device 10 in its next stage which may be considered as a stripping step in a stripping station. Before discussing the stripping step note is made of the general structure of device 10. Such structure includes a support or base 42 on which the various components are mounted. The components would include any suitable drive mechanism which includes encoder 44 which controls the longitudinal movement of holders 12,14 on support 42 in any suitable manner. The motor/encoder 44 could be connected to a lead screw 46 through a timing belt 48 for driving the tube holder 14 in a longitudinal direction. Tube holder 12 would also be driven in a longitudinal direction in any suitable manner. Preferably a carriage latch pin 49 extends transversely through the carriage for tube holder 14 and extends into an opening in the carriage for tube holder 12. FIG. 12A, which is the underside of device 10, shows the latch pin 49 urged by spring 51 into the engaging position to lock the carriage 15 for tube holder 14 to the carriage 13 for tube holder 12. Thus, when tube holder 14 is driven longitudinally it pulls tube holder 12 longitudinally with it. Tube holder 12, however, has associated with it a cam roller 50 which rides in track 52 to control the lateral position of tube holder 12 with respect to its adjacent tube holder 14. The longitudinal movement of tube holder 12 could be controlled by the movement of tube holder 14 in any other suitable manner or could be independent of tube holder 14. Joint longitudinal movement of both tube holders is preferred to assure proper positioning of the tube holders with respect to each other.

After the tubes T-1 and T-2 have been loaded and clamped, the tube holders 12,14 are moved together in a longitudinal direction to the stripping station. Simultaneously the tube holder 12 is moved laterally away from tube holder 14 by the cam roller 50 as a result of an outward bend in track 52. The lateral movement is shown by the arrow in FIG. 7. FIG. 7, as well as FIG. 5, illustrates the jaws 54 of clamp 18 to be square jaws (i.e. having a vertical back wall 54) while the jaws 56 of clamp 16 are smooth jaws (i.e. having a curved back wall 56). The compressed tubing is held tight by the square jaws 54 but the tubing is allowed to slip through the smooth jaws 56. As the tube holder 12 is laterally moved away from tube holder 14 any fluid is stripped from the weld site 40 prior to reaching the cutting blade. Thus, a comparison of FIGS. 5 and 7 show the size of the fluid free area or compressed portion 40 to increase in FIG. 7 as compared to the loading condition of FIG. 5.

As previously indicated the lateral position of tube holder 12 is controlled by cam roller 50 riding in cam track 52. Cam track 52 would be of any suitable shape and could include elongated portions 57,59 connected to each other by ramp 58. In the loading station shown in FIG. 2, for example, the cam roller 50 would be in the elongated portion 57 at a location which is innermost to dispose the tube holders and more particularly the clamps 16,18, into contact with each other as illustrated in FIG. 5. In the stripping station of FIG. 6 cam roller 50 moves to the location in elongated track portion 57 which would be slightly outward of the position in the loading station of FIG. 2. This would thereby cause the lateral shifting of tube holder 12.

FIGS. 8-11 illustrate device 10 when the components are moved to the cutting station where cam roller 50 is at the end of elongated track portion 57 which is also outwardly of the loading station position shown in FIG. 2. As a result, there is a sufficient spacing between the clamps 16,18 to accommodate the cutting blade 60. Cutting blade 60 is mounted on a cantilevered holder 62 as clearly shown in FIGS. 3 and 13. To reach the position shown in FIGS. 8-11 the tube holders 12,14 are driven together in a longitudinal direction by the lead screw 46 toward the cutting blade 60. The fluid free tubes in welding site 40 are cut with any suitable cutting device, such as a thin, cold custom razor blade. The tube holders 12,14 are now free to separate in the lateral direction prior to moving to the heat source 66 at the opposite end of support 42. As shown in FIG. 11, shim spacers 64 on each side of blade 60 are used to precisely center the blade during tube cutting.

After the tubes T-1 and T-2 have been cut four cut stub ends result, two from each of the tubes. Because the clamps are still in the clamped condition each of the stub ends is sealed and fluid free.

Figure 17:
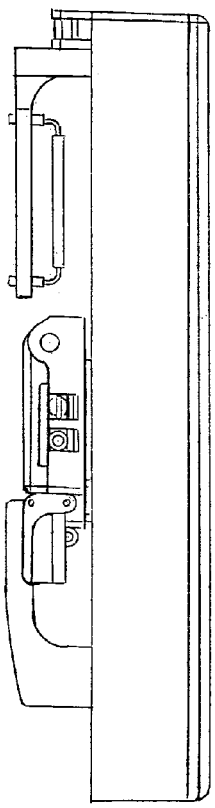
FIG. 17 is a side elevational view of the device shown in FIG. 16.
Figure 19:
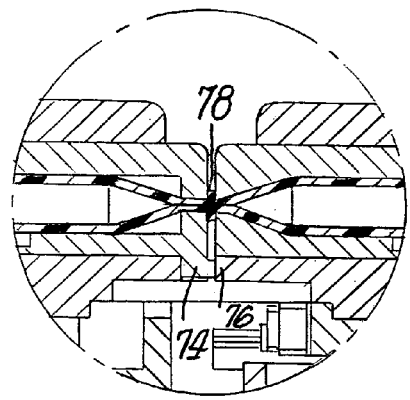
FIG. 19 is a view similar to FIGS. 5, 7, 11 and 15 showing the tubes in the welding station.
Figure 18:
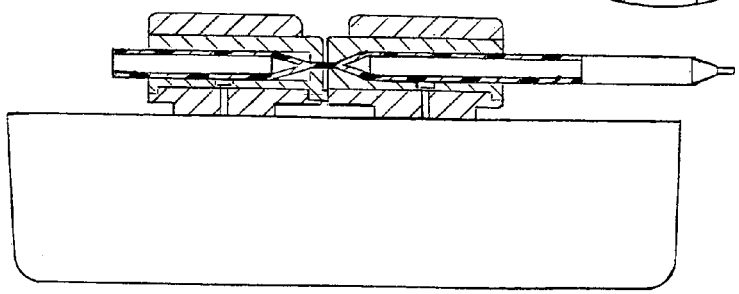
FIG. 18 is a cross-sectional view taken through FIG. 16 along the lines 18-18.

The next stage in the use of device 10 is the heating/melting stage. To reach this stage both tube holders 12,14 are driven in the reverse direction toward the heat source 66. FIGS. 12-15 show the components of device 10 when in the heating/melting station. As shown in FIGS. 3, 9 and 17 the heat source 66 is in the form of an infrared heat source mounted to a cantilevered support 68 located generally laterally centrally of the support 42. When the tube holders 12,14 are moved from the cutting station of FIG. 8 to the heating/melting station of FIG. 12 cam roller 50 enters the outer track portion 59 thus shifting tube holder 12 laterally away from tube holder 14 to create sufficient clearance for the heat source 66 to be located between the four stub ends of tubes T-1 and T-2. As the tube holders reach the final heat position the carriage latch pin 49 is pulled in by a cam 73 against the force of spring 51 which uncouples tube holders 12, 14 by withdrawing pin 49 from carriage 13. The tube holders 12,14 now pause to allow the cut tube ends or stubs to be heat sterilized and melted. As shown in FIGS. 2, 6 and 8 a heating position ball detent 70 is located at the heating/melting station. FIG. 14 illustrates the carriage for holder 12 to include a spring loaded ball plunger 72 which enters the detent 70 for indexing the tube holder carriages and maintaining them in a paused condition during heating/melting. The engagement of spring loaded ball plunger 72 in detent 70 also causes tube holder 12 to remain in the heating/melting station when the now uncoupled tube holder 14 begins to move away from the heating melting station, as later described.

Heat source 66 may be in continuous operation. Alternatively, through use of a timer, the heat source may be periodically turned off and activated only when necessary.

The next stage in the use of device 10 is the welding of a stub end of tube T-1 to a stub end of tube T-2 so that, for example, the bag 20 will be in communication with filter 32. FIGS. 16-19 illustrate the components of device 10 when in the welding station. First, after the tube ends or stubs are melted the motor 44 reverses direction and moves the tube holders 12,14 towards the final weld position. The tube holder 12 is held in place by spring loaded plunger 72 underneath the tube holder 12 and by the heat position ball detent 70. With the carriage latch pin 49 released the tube holder 14 is free to shift in the longitudinal direction with respect to the now stationary tube holder 12. As shown in FIG. 12A, a protruding tab 74 underneath the tube holder 14 and a corresponding slot 76 in the carriage 13 for the tube holder 12 establish the shift position. In other words, tube holder 14 moves free of tube holder 12 until the tab 74 contacts the end of slot 76.

Figure 16:
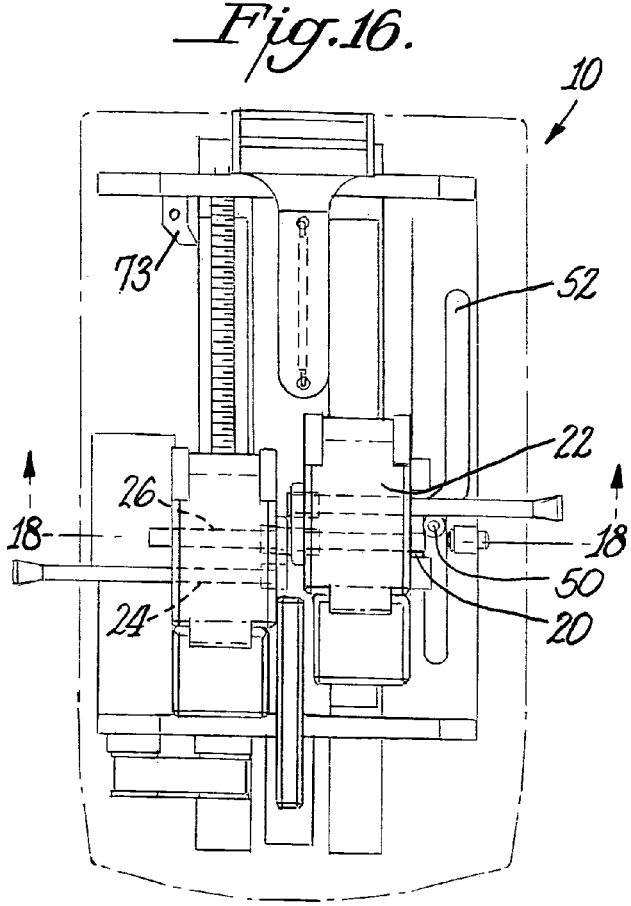
FIG. 16 is a top plan view of the device shown in FIGS. 1-15 in the welding station.

The engagement of the spring biased plunger ball 72 in the detent 70 after the tube holders have been uncoupled from each other might be considered as pausing structure releasably engaged with complementary pausing structure to maintain the first tube holder 12 longitudinally stationary while the independently movable second tube holder 14 moves longitudinally until protruding tab or projection 74 of second tube holder 14 contacts the end of the slot 76 in first tube holder 12. Continued movement of second tube holder 14 overcomes the force of plunger ball 72 in detent 70 to thereby release the plunger ball 72 from detent 70. The distance that second tube holder 14 moves longitudinally while first tube holder 12 is stationary is a fixed distance which corresponds or is the same as the center line to center line distance between the parallel tube holding areas of each tube holder to assure a realignment where first tube holding area 20 of first tube holder 12 is aligned with second tube holding area 26 of second tube holder 14. Thus, this longitudinal shifting of the tube holders 12,14 axially aligns the tube holding area 20 of tube holder 12 with the tube holding area 26 of tube holder 14 as shown in FIG. 16. The tube stubs in these slots 20,26 will then be welded together while the tube stubs in slots 22,24 will remain distinct from each other and will result in a pair of tube portions sealed at each end.

As the tube holders 12,14 move towards the final weld position the tube holder 12 laterally positioned by the cam roller 50 closes in until the final weld gap is reached. FIG. 16 shows cam holder 50 located in this portion of track 52 corresponding to the final weld position. The protruding tab 74 on the tube holder 14 which only engages the end of slot 76 when the tube holders are shifted to the precise position for welding allows the weld flange 78 to be accurate and reproduceable. The molten plastic quickly solidifies leaving two sealed stub ends and one connected tube. The clamps 16,18 can now be opened and the tubes removed. The flow in the welded tube is reestablished by squeezing the weld flange 78 to pop a thin plastic membrane remaining in the weld site.

FIGS. 2, 6, 8, 12A and 16 illustrate the carriage latch pin release cam 73 which releases the latch pin 49 to enable the tube holders 14,16 to move independently of each other. Latch pin 47 could extend through the carriage 15 of tube holder 14 in a lateral direction and into the carriage 13 of tube holder 12. Cam 73 would engage spring biased latch pin 49 when at the heating/melting station to pull latch pin 49 outwardly and away from tube holder 12 thereby unlatching the two tube holders.

After the welding has been completed and the welded tube and two sealed tube portions have been removed from the tube holders, the tube holders are again put in the condition for a next sequence of steps to form another welded tube. Tube holders 12,14 are shifted back to their original alignment condition. Carriage latch pin 49 again engages the carriage 13 for tube holder 12 and the coupled tube holders would be again at the loading station awaiting placement of the next set of tubes.

As previously indicated any suitable clamping mechanism can be used within the various practices of this invention. The clamping mechanism shown in FIGS. 1-19 are suitable for generally small diameter tubes where the clamping results from a downward pressing of an upper clamp member toward the lower clamp member to squeeze and compress the tube between the clamp jaws. FIGS. 20-25 show a clamp mechanism which would be particularly suitable for larger diameter tubes. As shown in FIGS. 20-25 the clamp 80 would be used with both tube holder 12,14. FIGS. 20-25 illustrate one such tube holder such as tube holder 12 which would include a pair of tube holding areas or parallel slots 20,22 which are clearly shown in FIG. 25 when the clamp 80 is in its open condition. The slots 20,22 would be suitably sized to be of a dimension for receiving a large diameter tube in each slot. A slidable rigid inverted T-shaped partition 82 is located between slots 20,22. A fixed rigid wall 84 is located at slot 20 with a corresponding laterally movable rigid wall 86 being at slot 22.

An actuating member 88 is hinged on tube holder 12 to pivot about pivot pin 90. When the actuator 88 is rotated in a clockwise direction slidable wall 86 and slidable partition 82 are moved laterally toward fixed wall 84 thereby vertically compressing the tubes T-1, T-2 as shown in FIG. 20.

The clamp 80 shown in FIGS. 20-25 could be provided on a separate device 10 or the clamps 16,18 could be detachable so that each can then be replaced by a clamp 80.

Although the weld 78 resulting from the welded tube sections could be opened under finger pressure, FIGS. 26-29 show a modified form of clamp 92 for mechanically opening the weld 78 which would be particularly desirable where a number of tubes are intended to be opened in a generally small time frame.

The weld opening features of clamp 92 could be incorporated in tube holder 12 and/or tube holder 14. FIGS. 26-29 show the features in tube holder 12. As shown therein tube holder 12 includes the slots 20,22 and includes top portion 34 hinged to bottom portion 36. As illustrated, the hinging or pivoting mechanism is accomplished through the use of a pair of posts 94 extending upwardly from bottom portion 36. The top portion includes a downwardly extending central section 96 of a size to fit between the posts 94. Central section 96 has a pair of outwardly extending shafts 98 fitting through corresponding holes in posts 96.

The weld opening structure particularly includes forming the curved outer surface of central section 96 with grooves or serrations 100 as best shown in FIG. 26. A pin 102 also extends outwardly from the rotating central section 96 toward serrated curved plate 101 mounted to bottom 36. After a pair of tube sections have been welded together at the weld flange 78, the welded tube sections are placed above pin 102 against the serrated surface 100 and serrated plate 101. The weld seam or flange 78 could be located at about the location of pin 102. Top portion 34 is then rotated from the open position shown in FIG. 26 to the closed position shown in FIG. 29. During the course of rotating the top portion 34 downwardly the welded tube sections are held in place against the gripping serrated surfaces 100 and 101. The rolling action squeezes and compresses the welded tube sections to pop open the weld 78 thereby forming communication completely through the region 79 that had contained the weld 78. Top portion 34 is then rotated in the reverse direction back to the open condition shown in FIG. 26 and the welded tube is removed from tube holder 12.

The mechanical opening of the weld seam might thus be considered as comprising a longitudinal pocket open at both ends for receiving the welded pieces. Such pocket would be formed by pin 102 and by central section 96 and by plate 101 of the clamp. A movable compressing member, such as surface 100, then presses the welded tube sections against a complementary compressing member, such as plate 101, to compress the welded tube portions. This squeezing of the tube portions drives the welded tube downwardly, pops open the weld seam and creates communication between the tube portions. This mechanical action is facilitated by providing gripping structure, such as serrations, on the compressing members 100 and 101.

This invention has been described in its preferred embodiment wherein a pair of tubes is located across aligned tube holding areas. The concepts of this invention, however, may be broadly practiced in other manners. For example, in its broad aspect one of the tube holders could include a pair of parallel tube holding areas while the other tube holder has only one tube holding area. Such arrangement might be used where it is intended to attach a device such as a bag or a container having fluid flowing through its tube to a tube of an unused device which does not yet have fluid and does not even require a sealed end of its tube. In such circumstance the tube having the fluid would be placed in the first tube holding areas of the first and second tube holders, but it would only be necessary for the other tube to be placed in the second tube holding area of a tube holder located where the tube holders are adjacent to each other. A clamp would be used on each tube holder having the fluid containing tube, but a clamp is not necessary for the other tube. Preferably, however, even when there is no fluid in the second tube, the second tube is clamped to conform its shape to the clamped first tube. The simplified device would include laterally relatively shifting the clamps for the one tube to increase the fluid free area, but such a shifting would not be absolutely necessary for the other tube. Similarly, the device would include cutting through the fluid containing tube, but the other tube need not be cut if it would already terminate at the location where the tube holders are adjacent to each other. The cut tube stubs of the one tube and the single exposed tube would be heated/melted and there would be a lateral shifting to weld one of the cut tube stubs with the other tube as previously described.

The device for welding plastic tubes of this invention has numerous advantages. Significantly, the device is waterless. The use of cold cutting should not create sterility problems because there should be no adhesion between the cold blade and the cold tube. Although a motor operated device has been described the device could be battery operated. If desired, a heat sink and cooling fan could be mounted to support 42. Such fan could remain on continuously. Alternatively during periods of inactivity the fan could be operated at a lower speed or be in a standby condition. Because there is no heated wafer, no smoke would result which would otherwise occur from plastic remaining on a wafer during melting.

The device can be operated with improved speed and no or minimal smoke and with minimal maintenance. The time of operation from load to finish could be about 10 seconds. Because there is no adhesion between the cold tube and the cold blade a blade could be indefinitely reusable.

An advantageous feature of this invention is that the fundamental layout of the design with the cutting blade at one end and the heater on the other end allows the use of the same cam driven drive and shift mechanism to be used for small tubing as well as large tubing. Thus, tube sizes in the range, for example, of ⅛ inch to ½ inch could be customized for end-user needs.

The transition between small and large tubing could be accomplished with a change in clamping methods and/or with a larger cutting blade and a change in heater orientation, but the required holder travel and shift distance would remain essentially the same.

Where small diameter tubing, e.g. 4 mm to 6.4 mm is used, the tubing is clamped in a horizontal direction as illustrated in FIG. 5, while larger diameter tubing, e.g. 6.5-13 mm could be clamped in a vertical direction as illustrated in FIG. 20.

Smaller tubing sizes could be heated with a single ceramic wire-wound rod infrared heat source mounted in the horizontal direction as shown, for example, in FIG. 3. Larger tubing could be heated with two side by side vertically mounted IR heaters. The infrared heat source could be designed for continuous operation where a 30 to 70 watts of heat energy will be actively cooled by an aluminum heat sink and fan.

The infrared heat source could operate at about 1750° F. (954° C.) which will produce peak IR wavelengths between 2 and 4 microns. This is also the IR segment that most plastics, including PVC and water have a high receptiveness. The surface bio-burden being composed of mostly water (90%) will efficiently absorb the IR energy, its temperature rapidly increasing and evaporating killing the bio-burden. When the PVC plastic absorbs the IR its surface temperature also increases continuing to kill the bio-burden and melt the plastic, creating an appropriately sized melt pool through absorption and conduction.

The jaws used in the preferred clamps are designed to have features that facilitate fluid stripping and produce an accurate weld gap during the welding process. Fluid stripping is accomplished by holding one side of the tube compressed and fixed with square jaws and then pulling away in the opposite direction with jaws that have a smooth radius back wall which allow the compressed tubing to slip through with minimum friction. One of the lower jaws, such as in holder 14, also has a projecting tab 74 which fits in a corresponding recess, such as slot 76 in the opposite side jaw of holder 12 that allows the clamps to come together completely flush when the clamps are aligned for tube loading. However, when the clamps shift for welding the tab interferes with the closing of the clamps and sets up an accurate and repetitive weld gap.

The two tube lines are preferably loaded parallel and facing opposite each other with the sealed ends protruding from the sides of the tube holders or clamps. After the two tube lines are stripped of fluid, cut and heated, they axially shift position and come together to complete the weld. A protruding tab 74 underneath the tube holder 14 in a corresponding precision machine slot 76 in the carriage 13 of tube holder 12 accurately establish the shift distance which is critical in making a strong weld especially for thin walled tubing.

The device 10 is capable of welding most thermoplastic medical grade tubing compositions at 80% of original tube strengths. The cycle time would be approximately 20 seconds, although could be as fast as about 10 seconds. Device 10 is compact and portable and could weigh approximately 5 pounds having a small footprint of 8 inches length by 5 inches width and 4 inches height. After welding the welded tube can be opened by finger pressure. It is possible for one technician to operate two units at a time with ease. In situ maintenance capability is also possible.

The compactness of the device 10 is achieved partially by locating the cutting station at one end of the support with the heating/melting station at the opposite end. The loading station is located between the cutting station and the heating/melting station. The stripping station is longitudinally between the loading station and the cutting station. The welding station would be generally in the same location as the loading station. Thus, the various sequence of steps begin with the loading station and end with the welding station which are generally at the same location on the support. In operation when the start switch is activated the holders 12, 14 would automatically assume their loading station position.

What is claimed is:

1. A device for welding plastic tubes comprising a tube loading station, a first tube holder having first and second parallel tube holding areas, a second tube holder having a first tube holding area in line with said first tube holding area of said first tube holder when said tube holders are in said tube loading station whereby a first tube may be placed in said aligned first tube holding areas across a location where said tube holders are adjacent each other and whereby a second tube may be placed in said second tube holding area at a location where said tube holders are adjacent each other, a tube clamp in each of said first tube holding areas of said tube holders for clamping the first tube to create a generally fluid free area of the first tube where said clamps are clamping against the first tube, at least one of said tube clamps being laterally movable with respect to the other of said tube clamps while said tube clamps are in the clamping condition to increase the length of the fluid free area of the first tube and to create an enlarged gap between said tube clamps at a stripping station, said tube holders being movable to a cutting station with said clamps maintained in the clamping condition, a non-heated cutting device in said cutting station located for cutting through the first tube at the gap between said tube clamps and being capable of cutting through the second tube at a location between said aligned second tube holding areas to create two cut stub ends from the cut first tubes and with the second tube having at least one stub end, said tube holders being movable to a heating/melting station with said clamps maintained in the clamping condition, a heating device in said heating/melting station for heating/melting the stub ends of the tubes, realigning structure for realigning the tube holding areas so that one of said tube holding areas of said first tube holder becomes aligned with a tube holding area of said second tube holder to dispose a heated/melted stub end of the first tube toward and in alignment with a heated/melted stub end of the second tube, and lateral shifting structure for moving the aligned stub ends of the first tube and the second tube into contact with each other and become welded together at a welding station.

2. The device of claim 1 wherein said second tube holder has a second tube holding area in line with said second tube holding area of said first tube holder at the location where said tube holders are adjacent each other in said loading station whereby a second tube may be placed in the aligned second tube holding areas so that two cut stub ends are created when the second tube is cut.

3. The device of claim 2 wherein one of said tube clamps is located at each of said tube holding areas.

4. The device of claim 3 wherein said cutting device comprises a cold cutting blade.

5. The device of claim 4 wherein said heating device comprises an infrared heat source.

6. The device of claim 4 wherein a cam is mounted to said first tube holder and moves in a cam track for controlling and varying the lateral position of said first tube holder with respect to said second tube holder.

7. The device of claim 6 wherein each of said clamps comprises an upper clamp member hinged to a lower clamp member, and aligned clamps having jaws with abutting faces for preventing fluid from being entrapped in the compressed tube between said clamps.

8. The device of claim 7 wherein each of said jaws of said clamps on said second tube holder has a square back wall, and each of said jaws of said clamps on said first tube holder has a smooth back wall.

9. The device of claim 6 wherein each of said clamps includes a sliding rigid partition between said parallel tube holding areas of its said tube holder, a rigid fixed outer wall at one of said parallel tube holding areas, a rigid sliding outer wall at the other of said parallel tube holding areas, and said partition and said sliding outer wall being movable toward said fixed outer wall in response to actuation of an activating mechanism for moving said partition and said sliding outer wall toward said fixed outer wall to compress the tubes located in said parallel tube holding areas.

10. The device of claim 6 wherein said tube holders are interconnected by a latch pin for joint longitudinal movement, and a disengaging mechanism located at said heating station for disengaging said latch pin to permit independent longitudinal movement of said tube holders.

11. The device of claim 10 wherein said second tube holder is power driven in a longitudinal direction and simultaneously pulls said first tube holder longitudinally when said tube holders are interconnected by said latch pin.

12. The device of claim 11 wherein said second tube holder includes a projection extending into an elongated slot in said first tube holder whereby said second tube holder is capable of moving longitudinally a fixed distance while said first tube holder remains stationary until said projection contacts an end of said slot in said first tube holder to cause said second tube holder to resume pulling said first tube holder longitudinally for joint longitudinal movement of said tube holders, and said fixed distance of independent movement of said second tube holder being the same as the center line to center line distance between said parallel tube holding areas to realign said holding areas of said tube holders.

13. The device of claim 12 wherein said first tube holder includes pausing structure releasably engageable with complementary pausing structure at said heating/melting station to hold said first holder stationary at said heating/melting station while aid second holder moves longitudinally until said projection contacts said end of said slot to release the engagement of said pausing structure with said complementary pausing structure.

14. The device of claim 6 wherein said cutting blade is mounted on a cantilevered support and said infrared heat source is mounted on a cantilevered support.

15. The device of claim 6 wherein each of said tube holding areas is a slot.

16. The device of claim 6 including a support on which said tube holders are mounted and on which said stations are located, said cutting station being longitudinally at one end of said support, said heating/melting station being longitudinally at an end of said support opposite said one end, said loading station being located longitudinally between said cutting station and said heating/melting station, said stripping station being longitudinally between said loading station and said cutting station, and said welding station being longitudinally between said stripping station and said heating/melting station.

17. The device of claim 1 including a support on which said tube holders are mounted and on which said stations are located, said cutting station being longitudinally at one end of said support, said heating/melting station being longitudinally at an end of said support opposite said one end, said loading station being located longitudinally between said cutting station and said heating/melting station, said stripping station being longitudinally between said loading station and said cutting station and said welding station being longitudinally between said stripping station and said heating/melting station.

18. The device of claim 1 wherein said cutting device is a cutting blade and said heating device is an infrared heat source.

19. The device of claim 1 wherein a cam is mounted to said first tube holder and moves in a cam track for controlling and varying the lateral position of said first tube holder with said second tube holder.

20. The device of claim 1 wherein said tube holders are interconnected by a latch pin for joint longitudinal movement, and a disengaging mechanism located at said heating station for disengaging said latch pin to permit independent longitudinal movement of said tube holders.

21. The device of claim 20 wherein said second tube holder is power driven in a longitudinal direction and simultaneously pulls said first tube holder longitudinally when said tube holders are interconnected by said latch pin.

22. The device of claim 21 wherein said second tube holder includes a projection extending into an elongated slot in said first tube holder whereby said second tube holder is capable of moving longitudinally a fixed distance while said first tube holder remains stationary until said projection contacts an end of said slot in said first tube holder to cause said second tube holder to resume pulling said first tube holder longitudinally for joint longitudinal movement of said tube holders, and said fixed distance of independent movement of said second tube holder being the same as the center line to center line distance between said parallel tube holding areas to realign said holding areas of said tube holders.

23. The device of claim 22 wherein said first tube holder includes pausing structure releasably engageable with complementary pausing structure at said heating/melting station to hold said first holder stationary at said heating/melting station while aid second holder moves longitudinally until said projection contacts said end of said slot to release the engagement of said pausing structure with said complementary pausing structure.

24. The device of claim 1 wherein at least one of said tube holders includes mechanical structure for opening the weld seam of two welded tube portions, said mechanical structure comprising a longitudinal pocket for receiving the welded tube portions and compressing members for pressing against the welded seam while the welded seam is in the longitudinal pocket.

25. The device of claim 24 wherein said tube holder includes a bottom portion and a top portion hinged to said bottom portion, said top portion having a central section which includes a gripping surface, a pin mounted to said central section below at least a portion of said central section gripping surface, a plate mounted to said bottom portion having a gripping surface disposed toward said central section, said central section and said plate comprising said compressing members, and said central section and said plate and said pin forming said pocket.

* * * * *